(12) United States Patent
Stenzler et al.

(10) Patent No.: US 11,033,692 B2
(45) Date of Patent: Jun. 15, 2021

(54) FLAVORING ELEMENT FOR AN INHALATION DEVICE

(71) Applicant: Philip Morris Products S.A., Neuchatel (CH)

(72) Inventors: Alex Stenzler, Long Beach, CA (US); Steve Han, Huntington Beach, CA (US); Arthur Slutsky, Toronto (CA); Steven Ellis, Ontario (CA); Noe Zamel, Toronto (CA); Bildad Nyambura, Reading (GB)

(73) Assignee: Philip Morris Products S.A., Neuchatel (CH)

( * ) Notice: Subject to any disclaimer, the term of this patent is extended or adjusted under 35 U.S.C. 154(b) by 237 days.

(21) Appl. No.: 15/566,426

(22) PCT Filed: Apr. 13, 2016

(86) PCT No.: PCT/US2016/027255
§ 371 (c)(1),
(2) Date: Oct. 13, 2017

(87) PCT Pub. No.: WO2016/168276
PCT Pub. Date: Oct. 20, 2016

(65) Prior Publication Data
US 2018/0147371 A1    May 31, 2018

Related U.S. Application Data

(60) Provisional application No. 62/148,030, filed on Apr. 15, 2015.

(51) Int. Cl.
*A61M 15/00* (2006.01)
*A24F 47/00* (2020.01)
*A61M 15/06* (2006.01)

(52) U.S. Cl.
CPC ....... *A61M 15/0003* (2014.02); *A24F 47/002* (2013.01); *A61M 15/0036* (2014.02);
(Continued)

(58) Field of Classification Search
CPC .......... A61M 15/0001; A61M 15/0003; A61M 15/0005; A61M 15/0021; A61M 15/0036;
(Continued)

(56) References Cited

U.S. PATENT DOCUMENTS

| 5,167,242 A | 12/1992 | Turner et al. |
| 5,441,060 A | 8/1995 | Rose et al. |

(Continued)

FOREIGN PATENT DOCUMENTS

| CN | 101631583 A | 1/2010 |
| CN | 103068266 A | 4/2013 |

(Continued)

OTHER PUBLICATIONS

Extended EP Search Report for EP 16780608, issued by the European Patent Office dated Jan. 14, 2019; 8 pgs.
(Continued)

*Primary Examiner* — Jan Christopher L Merene
*Assistant Examiner* — Brian T Khong
(74) *Attorney, Agent, or Firm* — Mueting Raasch Group (57) ABSTRACT

A device for adding a flavor and/or cough suppressant component to an inhaler is described. The device includes a housing having an interior chamber, wherein the housing includes at least one air inlet and at least one air outlet connected to the interior chamber, thereby forming an airflow pathway through the interior chamber, and at least one flavoring and/or cough suppressant component positioned within the interior chamber, wherein the housing is attachable to an exterior surface of an inhaler having at least one air inlet, such that the at least one air outlet of the device (Continued)

aligns with the at least one air inlet of the inhaler to form an airflow path through the device and into the inhaler.

16 Claims, 6 Drawing Sheets

(52) U.S. Cl.
CPC ......... *A61M 15/06* (2013.01); *A61M 15/0041* (2014.02); *A61M 2202/064* (2013.01); *A61M 2206/18* (2013.01)

(58) Field of Classification Search
CPC .............. A61M 15/06; A61M 15/0041; A61M 15/0016; A61M 15/0028; A61M 15/003–0041; A61M 2205/128; A61M 11/002; A61M 11/08; A24F 47/002; A24F 47/00; A24F 47/008; A24F 47/004; A24F 47/006; A24D 1/002; A61L 9/125
See application file for complete search history.

(56) References Cited

U.S. PATENT DOCUMENTS

| | | | |
|---|---|---|---|
| 6,234,169 B1* | 5/2001 | Bulbrook | A61M 15/06 128/203.12 |
| 6,478,633 B1* | 11/2002 | Hwang | H01R 4/06 439/287 |
| 6,578,571 B1 | 6/2003 | Watt | |
| 7,204,247 B1* | 4/2007 | Rogerson | A61M 15/009 128/200.23 |
| 8,215,300 B2 | 7/2012 | Steiner et al. | |
| 9,986,765 B2* | 6/2018 | Batista | A24F 47/008 |
| 2001/0010223 A1* | 8/2001 | Gonda | A61M 15/00 128/200.14 |
| 2002/0073991 A1* | 6/2002 | Gonda | A61M 15/00 128/200.22 |
| 2005/0051166 A1* | 3/2005 | Glusker | A61M 15/0028 128/203.21 |
| 2005/0067503 A1* | 3/2005 | Katase | A61M 15/02 239/373 |
| 2007/0267032 A1 | 11/2007 | Shan | |
| 2008/0142010 A1* | 6/2008 | Weaver | A61M 11/041 128/203.26 |
| 2008/0202514 A1* | 8/2008 | Kriksunov | A61M 15/0065 128/203.15 |
| 2008/0230053 A1 | 9/2008 | Kraft et al. | |
| 2009/0090361 A1* | 4/2009 | Gumaste | A61M 15/0028 128/203.15 |
| 2009/0151717 A1* | 6/2009 | Bowen | A61M 11/048 128/200.23 |
| 2009/0277928 A1* | 11/2009 | Bruckner | B05B 11/0078 222/129 |
| 2009/0308390 A1 | 12/2009 | Smutney et al. | |
| 2011/0120455 A1* | 5/2011 | Murphy | A24F 47/002 128/200.18 |
| 2011/0220234 A1* | 9/2011 | Haas | A61M 15/0028 138/109 |
| 2012/0145150 A1* | 6/2012 | Donovan | A61M 15/0028 128/203.15 |
| 2012/0160241 A1* | 6/2012 | Oliva | A61M 15/0028 128/203.15 |
| 2013/0074857 A1* | 3/2013 | Buchberger | A61M 15/06 131/329 |
| 2013/0160779 A1* | 6/2013 | Chida | A24B 15/14 131/329 |
| 2013/0160780 A1* | 6/2013 | Matsumoto | A24F 47/002 131/329 |
| 2013/0192620 A1* | 8/2013 | Tucker | H01C 17/00 131/329 |
| 2013/0276781 A1 | 10/2013 | Steelman et al. | |
| 2013/0298921 A1* | 11/2013 | Williams | A24B 15/16 131/270 |
| 2014/0048062 A1* | 2/2014 | Faram | A61M 11/00 128/200.18 |
| 2014/0088045 A1 | 3/2014 | Rigas et al. | |
| 2014/0116426 A1* | 5/2014 | Mullinger | A61M 15/0071 128/200.14 |
| 2014/0144429 A1* | 5/2014 | Wensley | A61M 15/06 128/200.14 |
| 2014/0261474 A1* | 9/2014 | Gonda | A61M 15/06 131/270 |
| 2015/0027456 A1* | 1/2015 | Janardhan | A24F 47/008 131/328 |
| 2015/0144129 A1* | 5/2015 | Djupesland | A61M 15/08 128/200.23 |
| 2015/0174360 A1* | 6/2015 | Stenzler | A61M 16/127 128/203.12 |
| 2015/0237913 A1* | 8/2015 | Suzuki | A24F 47/004 131/329 |
| 2015/0297845 A1* | 10/2015 | Shahaf | A61M 15/08 128/200.23 |
| 2015/0335062 A1* | 11/2015 | Shinkawa | A24B 15/10 131/276 |
| 2016/0022930 A1* | 1/2016 | Greim | A61M 15/06 131/328 |
| 2016/0045682 A1* | 2/2016 | Boyden | A61M 15/0068 128/200.19 |
| 2017/0035107 A1* | 2/2017 | Zinovik | A61M 15/06 |
| 2017/0042251 A1* | 2/2017 | Yamada | A24F 47/00 |
| 2017/0135397 A1* | 5/2017 | Buehler | A24F 47/002 |

FOREIGN PATENT DOCUMENTS

| | | | | |
|---|---|---|---|---|
| EA | 009895 B1 | 4/2008 | | |
| EP | 2609822 A1 | 7/2013 | | |
| EP | 2792256 B1 | 6/2017 | | |
| JP | 31-5390 Y | 4/1956 | | |
| JP | S62-175896 U | 11/1987 | | |
| JP | 2002-522173 A | 7/2000 | | |
| RU | 2468832 C2 | 12/2012 | | |
| WO | WO 00/09188 A1 | 2/2000 | | |
| WO | WO 2007/088425 A2 | 8/2007 | | |
| WO | WO 2013/111320 A1 | 8/2013 | | |
| WO | WO 2013/133903 A1 | 9/2013 | | |
| WO | WO-2014089174 A2 * | 6/2014 | ......... | B05B 11/0054 |
| WO | WO 2015/166350 A2 | 11/2015 | | |
| WO | WO 2015/193498 A1 | 12/2015 | | |

OTHER PUBLICATIONS

International Search Report and Written Opinion for PCT/US2016/027255, issued by the U.S. Patent and Trademark Office dated Jul. 18, 2016; 10 pgs.

International Preliminary Report on Patentability for PCT/US2016/027255, issued by the International Bureau of WIPO dated Oct. 26, 2017; 10 pgs.

Polverino et al., "Anatomy and neuro-pathophysiology of the cough reflex arc," *Multidisc Resp Med*, Jun. 18, 2012;7(1): 5 pgs.

Japanese Office Action issued in corresponding JP Application No. 2018-505572, dated Feb. 10, 2020; 7 pages including English Translation.

Russian Office Action and Search Report for Application No. 2017136816, issued by the Federal Service for Intellectual Property; dated Sep. 17, 2019; 11 pages, including English Translation.

Chinese Office action issued by the National Intellectual Property Administration, dated Feb. 3, 2020, 20 pages including English Translation.

Japanese Office Action for JP 2018-505572, issued by the Japanese Patent Office dated Oct. 8, 2020, 6 pgs including English translation.

* cited by examiner

FLAVORING ELEMENT FOR AN INHALATION DEVICE

CROSS-REFERENCE TO RELATED APPLICATIONS

This application is a national stage entry of PCT/US16/27255 filed on Apr. 13, 2016, which claims priority to U.S. provisional application No. 62/148,030 filed on Apr. 15, 2015 both of which are incorporated herein by reference in their entireties.

BACKGROUND OF THE INVENTION

Inhaling powder nicotine has become an effective and popular way to deliver nicotine to the bloodstream while reducing the hazardous effects of smoking. Unpleasant odors and the hazardous effects of second hand smoke are just some of the effects that can be avoided by using a dry powder inhaler over a traditional cigarette. Conventional dry powder nicotine formulations may be substantially flavorless, or otherwise have a subtle or consequential flavor that may not be desired by the user. In addition, some users may prefer to introduce a particular flavor or a generally appealing that will taste pleasant during inhalation.

It is known in the art that flavored particles can be mixed into a dry powder formulation and inhalation device as a composition with the active ingredient, such that the flavored element aerosolizes with the active ingredient during inhalation for a more pleasant taste (see for example P.C.T. Publication No. WO 2013133903 to Kamler et al. and U.S. Patent Publication No. 2007/0267032 to Shan). However, once a particular flavor is pre-mixed with the active ingredient, the user cannot switch to a different flavor without replacing the entire mixture, potentially wasting the medicament. Likewise, if the user wants to switch to a flavorless taste, the same wasteful result would occur since the flavored elements cannot be later removed from the active ingredient.

Further, a typical smoker often experiences an increase in coughing. Coughing is a reflex triggered in order to clear the airways of secretions and particulates (Polverino et al., Multidiscip Respir Med. 2012; 7(1): 5). Among other causes, coughing can be triggered by mechanical or chemical stimulants on cough receptors found in various parts of the human airways such as trachea, branching points of large airways, pharynx and larynx. At a minimum, coughing can be an unpleasant side effect which the smoker may negatively associate with a nicotine formulation, or smoking cessation treatment. But at the same time, coughing may also render a treatment ineffective by expelling inhaled nicotine formulation particles outside of the airways. An effective formulation for the treatment of nicotine addiction should ideally be able to deliver to the airways of the smoker enough of a nicotine formulation in a form and concentration that will mimic the effects of cigarette smoking, while at the same time controlling and suppressing the coughing reflex.

Menthol is a known and widely used topical analgesic, decongestant and cough suppressant. Almost all cigarettes contain menthol in order to adjust flavoring and reduce coughing. When the menthol concentration in cigarettes exceeds 3%, then it is labeled as a menthol cigarette. Methods of using menthol in cigarettes include addition to the tobacco leaf. A plastic ball filled with menthol can be stored in the filter of a cigarette, and then crushed prior to smoking the cigarette. Upon lighting up the cigarette, the heated smoke acts to volatilize and carry the menthol into the airways of the smoker.

But adding menthol to dry powder formulations of nicotine raises several challenges in terms of the effectiveness of the final product. Of particular interest is the effectiveness of menthol in reaching the cough receptors of the smoker. If the menthol particles hit a lesser number of receptors than the nicotine particles, then the effectiveness of menthol in suppressing cough will be at best attenuated, or even inexistent.

Thus, there is a need in the art for improved devices and methods for optionally incorporating a flavor and/or cough suppressant component via an inhalation device, such that the user has a high level of flexibility and option as to what additional compounds are added or removed during the course of administering all or a portion of the active ingredient. The present invention satisfies this need.

SUMMARY OF THE INVENTION

A device for adding a flavor component to an inhaler is described. The device includes a housing having an interior chamber, wherein the housing includes at least one air inlet and at least one air outlet connected to the interior chamber, thereby forming an airflow pathway through the interior chamber, and at least one flavoring component positioned within the interior chamber, wherein the housing is attachable to an exterior surface of an inhaler having at least one air inlet, such that the at least one air outlet of the device aligns with the at least one air inlet of the inhaler to form an airflow path through the device and into the inhaler.

Also described is a dry powder inhaler. The inhaler includes a first housing having a proximal end, a distal end and a length therebetween, wherein the housing defines an internal passage having proximal, intermediate and distal regions along the first housing length, a proximal end opening, a distal end opening and proximal region opening each in connection with the internal passage, a dry powder medicament compartment within the distal region of the internal passage, a powder fluidization and deagglomeration apparatus within the intermediate region of the internal passage, and a second housing having an interior chamber, wherein the second housing includes at least one air inlet and at least one air outlet connected to the interior chamber, thereby forming an airflow pathway through the interior chamber, and at least one flavoring component positioned within the interior chamber, wherein the at least one air outlet of the second housing aligns with the proximal region opening of the first housing when the second housing engages the first housing.

Also described is a method for dry powder inhalation. In certain embodiments, the method includes the steps of providing a dry powder inhaler including a proximal end having a proximal opening, a distal end, and shaft wall extending from the proximal end to the distal end, a first compartment configured to hold a dry powder, a pathway connected to the first compartment by a first opening, the pathway including the proximal opening, and a second opening in the shaft wall connected to the pathway. In certain embodiment, the method provides a housing attachable to the shaft wall and configured to at least partially cover the second opening, the housing having first and second housing openings and at least one flavoring or cough suppressant component. The method may also include the step of generating a negative pressure at the proximal opening such that a portion of the dry powder exits the first compartment and enters the pathway, a portion of the at least one flavoring or cough suppressant component exits the housing and enters the pathway through the second opening, and the portion of the dry powder and the portion of the at least one flavoring or cough suppressant mix in an airflow generated by the negative pressure.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

Figure 1:
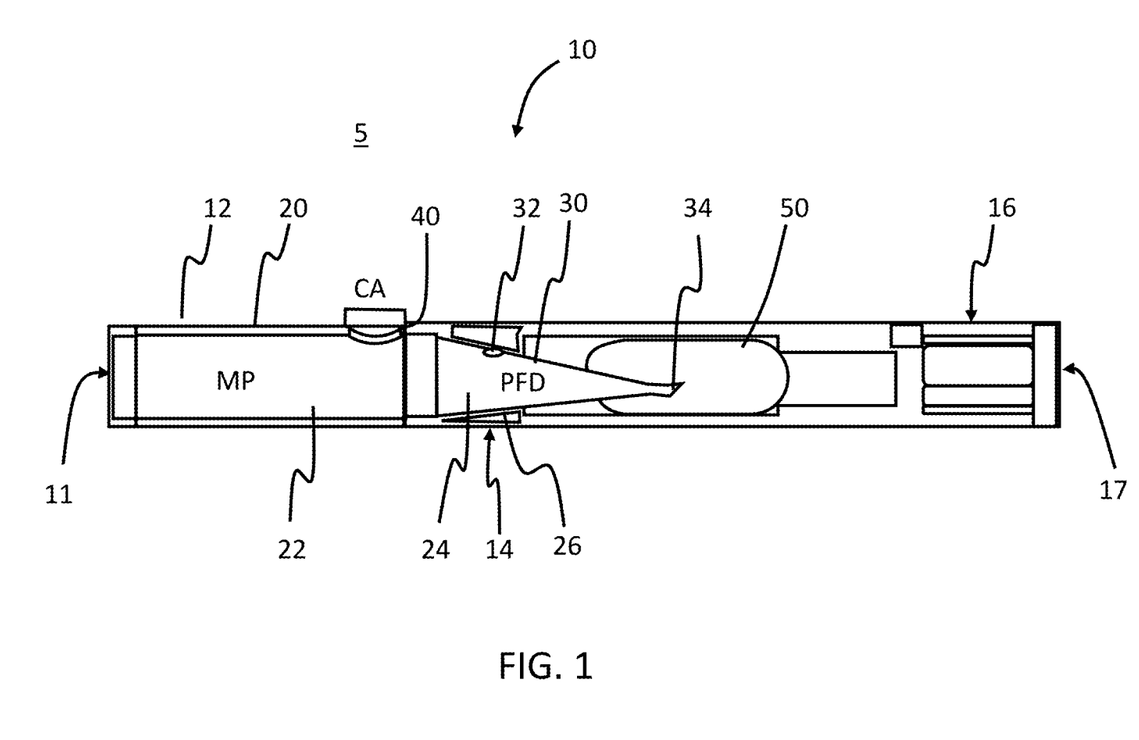
Figure 2:
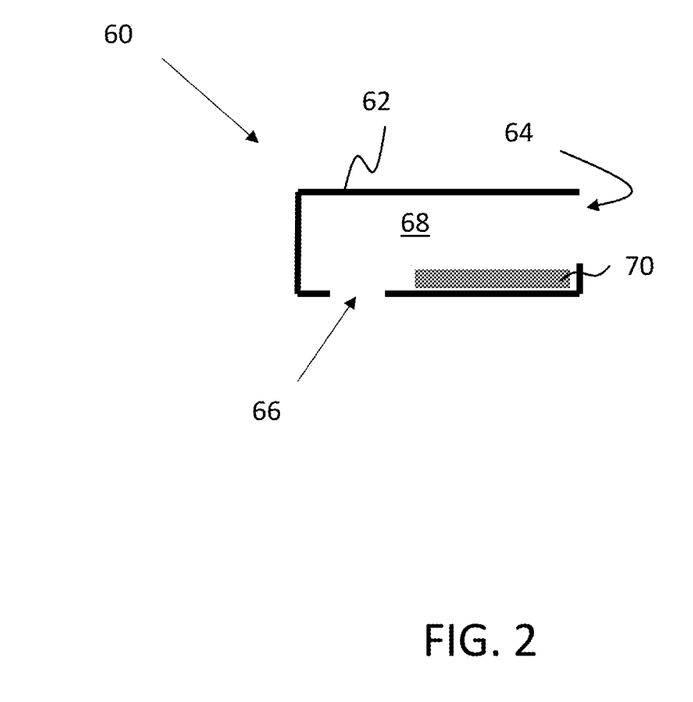

FIG. 1 is a cross sectional view of an exemplary dry powder inhaler.

FIG. 2 is a cross sectional view of an exemplary attachable flavoring and/or cough suppressant compartment.

FIG. 3 is a cross sectional view of an exemplary dry powder inhaler having a flavoring or cough suppressant compartment attached thereto.

FIG. 4 is a cross sectional view of another exemplary dry powder inhaler having a flavoring or cough suppressant compartment attached thereto.

FIG. 5 is a cross sectional view of yet another exemplary dry powder inhaler having a flavoring or cough suppressant compartment attached thereto.

FIG. 6 is a photograph of an exemplary flavoring or cough suppressant compartment attached to an inhaler.

FIG. 7 is a picture of an exemplary cylindrical flavoring or cough suppressant compartment insertable into an opening of an inhaler.

DETAILED DESCRIPTION OF THE INVENTION

The present invention can be understood more readily by reference to the following detailed description, the examples included therein, and to the Figures and their following description. The drawings, which are not necessarily to scale, depict selected embodiments and are not intended to limit the scope of the invention. The detailed description illustrates by way of example, not by way of limitation, the principles of the invention. The skilled artisan will readily appreciate that the devices and methods described herein are merely examples and that variations can be made without departing from the spirit and scope of the invention. It is also to be understood that the terminology used herein is for the purpose of describing particular embodiments only and is not intended to be limiting. It is to be understood that the figures and descriptions of the present invention have been simplified to illustrate elements that are relevant for a more clear comprehension of the present invention, while eliminating, for the purpose of clarity, many other elements found in systems and methods of providing flavoring and/or cough suppressant compounds for an inhalation device. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

As used herein, the term "dry powder" refers to a fine particulate composition that is not suspended or dissolved in a propellant, carrier, or other liquid, and it is not meant to necessarily imply a complete absence of all water molecules.

Unless stated otherwise, the described size or size range of a particle should be considered as the mass median aerodynamic diameter (MMAD) of the particle or set of particles. Such values are based on the distribution of the aerodynamic particle diameters defined as the diameter of a sphere with a density of 1 $gm/cm^3$ that has the same aerodynamic behavior as the particle which is being characterized. Because the particles described herein may be in a variety of densities and shapes, the size of the particles is expressed as the MMAD and not the actual diameter of the particles.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is a flavoring and/or cough suppressant compartment suitable for use in conjunction with an inhalation device, such as may be used for inhalation of nicotine based formulations.

With reference to FIG. 1, the dry powder inhaler or device 10 is formed from a housing 20 in the form of a shaft extending from a proximal end 12 to a distal end 16. Preferably, the housing 20 may form a generally cylindrical shape, similar to a conventional cigarette. In alternative embodiments, the device housing can form any other desired shape, such as substantially rectangular, triangular, trapezoidal or any other shape, as will be appreciated by those having ordinary skill in the art. The proximal tip of the device 10 has a round opening 11, forming a mouthpiece (MP) that allows a user to inhale through the opening 11 and generate a negative pressure at the proximal end 12 of the device 10. It should be appreciated that opening 11 may be any shape desired, such as oval, or a narrowed slit. Preferably, opening 11 is ergonomically shaped or contoured in conjunction with the proximal end of the MP to fit comfortably within the subject's mouth. An intermediate region 14 of device 10 includes a powder fluidization and deagglomeration apparatus (PFD) positioned within an interior chamber 26 of the device housing 20. The PFD may be integrated with the interior surface of housing 20 as a single unit, or the PFD may be a separate component that is removable from the interior of housing 20. The PFD also has a housing wall 30 forming an internal chamber 24. The PFD further includes an opening 34 at its distal end which may further serve as a piercing component for piercing a container of dry powder, such as dry powder capsule 50. Opening 34 includes a channel into internal chamber 24, such that an air passage is created between the inside of capsule 50 and internal chamber 24 of the PFD. Alternatively, opening 34 of the PFD may be positioned to access a dry powder reservoir within housing 20. As contemplated herein, the PFD housing wall 30 can form a number of geometries defining internal chamber 24, including a tapered geometry forming a frusto-conical chamber 24, as shown in FIG. 1. Functionally, the PFD provides powder fluidization, or entraining powder in the air stream, and for reducing fluidized powder suspended in the air stream to at or near primary particle state. The distal end 16 of device 10 terminates in an opening 17 that in certain embodiments, can be removable and/or be covered by a filter.

When a negative pressure is applied to the proximal passage 22 of the MP, air is pulled from the external environment 5 through opening 17 at the distal end 16 of device 10 and past the capsule 50 or other powder reservoir into internal chamber 26 of device 10. This air is then further pulled through an opening 32 within wall 30 of the PFD housing and into internal chamber 24 of the PFD. A portion of the air entering the chamber 24 via chamber opening 32 flows directly towards the proximal opening 11, forming a primary airflow. Additionally, the low pressure area at the distal end of internal chamber 24 creates a secondary airflow directed towards this distal end region of internal chamber 24. The decreasing cross-sectional area of chamber 24 in the distal direction causes a burst of secondary airflow which enters the pierced capsule and scours the surface of powder in the capsule, entraining a small portion of powder before rejoining the primary airflow traveling proximally towards opening 11 for inhalation by the user. Alternatively, instead of (or in addition to) opening 32, PFD housing wall 30 may include any shape or geometry suitable for generating an air passage or hole within the capsule wall when punctured, such that air may flow directly from chamber 26 into the capsule. Device 10 can be used to inhale a dry powder formulation that is positioned directly into a powder reservoir chamber, or that is contained within a capsule or other separate packaging that can be placed within device 10.

An opening 40 in the housing wall 20 of the MP opens into passage 22 provides a passageway between the proximal passage 22 and the external environment 5. Accordingly, in one embodiment, the opening 40 (or CA) can serve as a chase airflow pathway, such that the velocity of the airborne powder particles drawn into the MP by the PFD can be increased and delivered deep into the lungs, instead of settling in the MP and user's mouth.

In certain embodiments, the inhalation devices described herein may be used to deliver a medicament, such as dry powder formulations of nicotine, and optionally other selected materials contained within a storage chamber, such as a capsule. For example, in one embodiment, the formulation includes nicotine particles (also referred to herein as the nicotine-based component) sized substantially between 1-10 microns, based on the MMD of the particles.

Further included is a detachable compartment 60 suitable for containing at least one flavoring and/or cough suppressant component therein, as shown in isolation in FIG. 2. Compartment 60 is formed from a housing 62 that may include at least one air inlet opening 64, at least one air outlet opening 66 and at least one flavoring and/or cough suppressant component 70 positioned at least partially within an interior chamber 68 of housing 62. Housing 62 may be any shape, size or geometry desired, without limitation.

Flavoring and/or cough suppressant component 70 may be a loose composition, such as a powder, or it may be a liquid composition within a pad or wick, such that at least a portion of the liquid composition may go through a phase transition to form a vapor within chamber 68. It should be appreciated that there is no limitation to the type of flavoring and/or cough suppressant component, to the containment mechanism of the flavoring and/or cough suppressant component, or to the release of any portion of the flavoring and/or cough suppressant component within chamber 68.

In another embodiment, component 70 may be or include a flavor component. In one embodiment, the flavor component is menthol. In another embodiment, the flavor component is vanilla. In other embodiments, the flavor component may include tobacco, fruit flavors, or food grade flavorings used in candy or baking. It should be appreciated that the flavor compound may be any flavoring compound known in the art, preferably a regulatory-approved flavoring compound. This flavor component may impact the subject in the oral cavity during use of the devices described herein to produce a desired flavor, as the flavor component particles may be limited in their ability to enter into the subject's lungs.

In one embodiment, component 70 may be or include a cough suppressant component. In one embodiment, the cough suppressant component is menthol. In another embodiment, the cough suppressant component may include benzocaine. It should be appreciated that the cough suppressant component can include any compound approved for suppressing cough. In embodiments where the component is menthol, cough may be reduced by soothing irritation in the subject's upper airways via menthol particles contacting the upper airways of the subject when inhaled via the devices described herein. In another embodiment, the cough suppressant component may also reduce a cough caused by irritation of the oro-pharynx, the glottis vocal cords and other anatomic regions more proximal or closer to the mouth that contain receptors that can trigger cough or trigger other unwanted sensations. As contemplated herein, the cough suppressant component may be formulated such that it is substantially prohibited from entering the sub-glottic airways. It should be appreciated that the cough suppressant component may act to dilute the medicament component and decrease cough caused by nicotine irritating the oro-pharynx, vocal cords and other anatomic regions proximal to the trachea.

Accordingly, the devices and methods presented herein represent a novel product and approach to delivery of dry powder nicotine-based formulations with optional or customized flavoring and/or cough suppressant components. Unlike existing technologies which do not separate or segregate material components according to size, composition or other parameter, the present invention selectively controls the combination of components delivered to the subject at the time of use according to user selection. Accordingly, a unique and superior product is presented that delivers respirable nicotine to the alveoli and small airways while optionally delivering a cough suppressant to the larger airways and/or the oro-pharynx, as well as optionally delivering flavor particles to the oral cavity.

Figure 3:
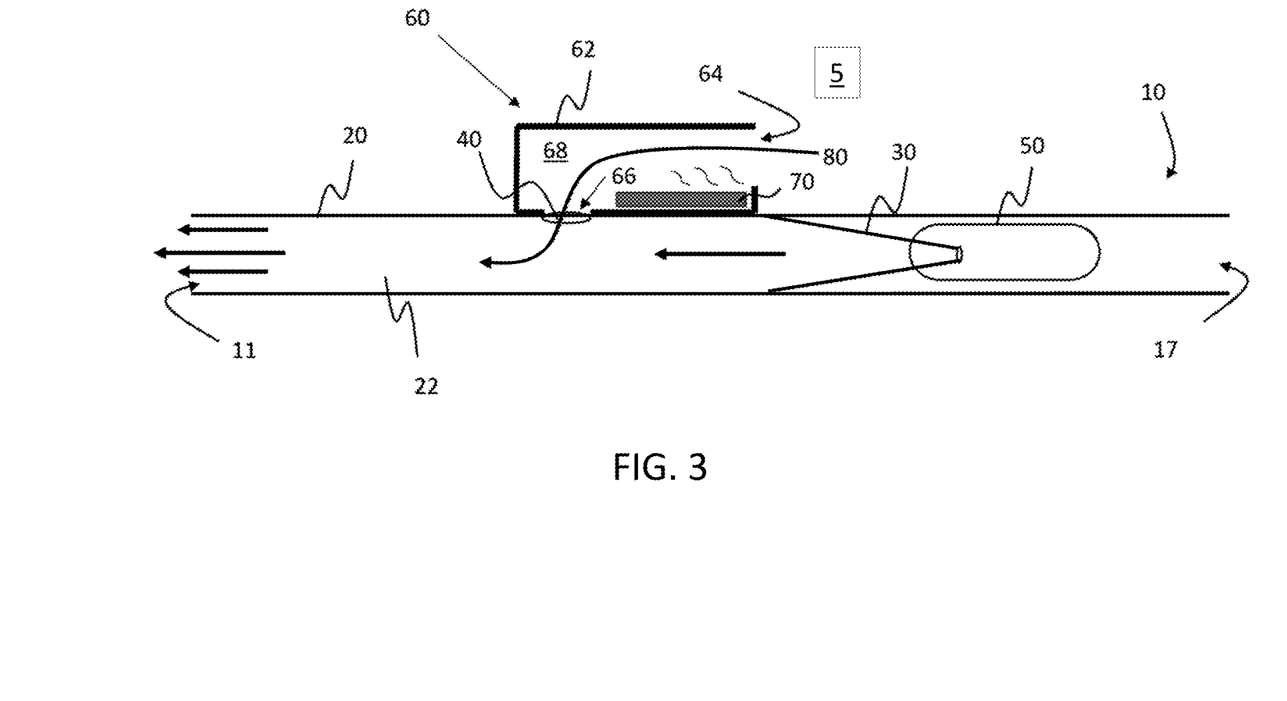

In the exemplary embodiment shown in FIG. 3, a more simplified dry powder inhaler 10 is shown, with compartment 60 releasably attached thereto. As shown, compartment 60 is positioned on the exterior surface of housing 20, such that the at least one air outlet 66 is positioned over opening 40 of housing 20, thereby allowing an airflow path 80 to permit air from the external environment 5 to be drawn through inlet opening 64 into chamber 68 and through opening 40 into proximal passage 22 of device 10. In certain embodiments, the compartment 60 clips onto the outer surface of housing 20 using a snap-fit or similar mating configuration for temporary engagement of compartment 60 to device 10. Alternative securement methods known in the art may also be used, such as a snap or other friction fit, spring tension, ties, adhesives, screw-in or magnetic securement. It should be appreciated that there is no limitation to the type of engagement mechanism for attaching compartment 60 to device 10. While the flavoring and/or cough suppressant compartment is generally described herein as being attachable and detachable, in other embodiments the flavoring and/or cough suppressant compartment may be permanently affixed to at least a portion of housing 20 of device 10.

During inhalation, airflow along flow path 80 passes across the flavoring and/or cough suppressant component 70, such that at least a portion of the flavoring and/or cough suppressant component (either as a vapor or other particle) is released into chamber 68 and pulled into proximal passage 22 during inhalation at the mouthpiece opening 11. Accordingly, when device 10 also has a capsule 50 engaged by the PFD, the medicament within capsule 50 is drawn into proximal passage 22, admixed with the flavoring and/or cough suppressant component 70 drawn from compartment 60, and delivered to the patient as a mix of medicament and flavoring and/or cough suppressant component. It should be appreciated that the flavoring and/or cough suppressant component may be delivered in this manner either as a mix with the medicament, as described above, or it may be delivered separately from the medicament, such as shortly before medicament delivery or shortly after medicament delivery, as desired by the subject.

Figure 4:
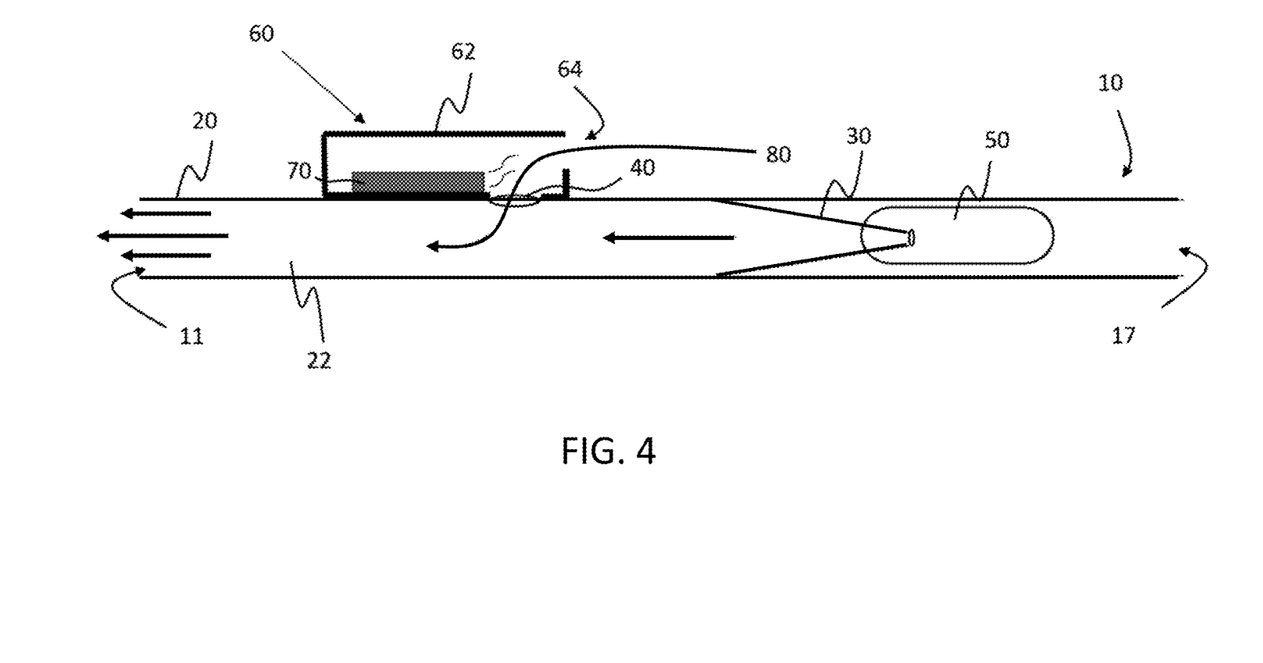
Figure 5:
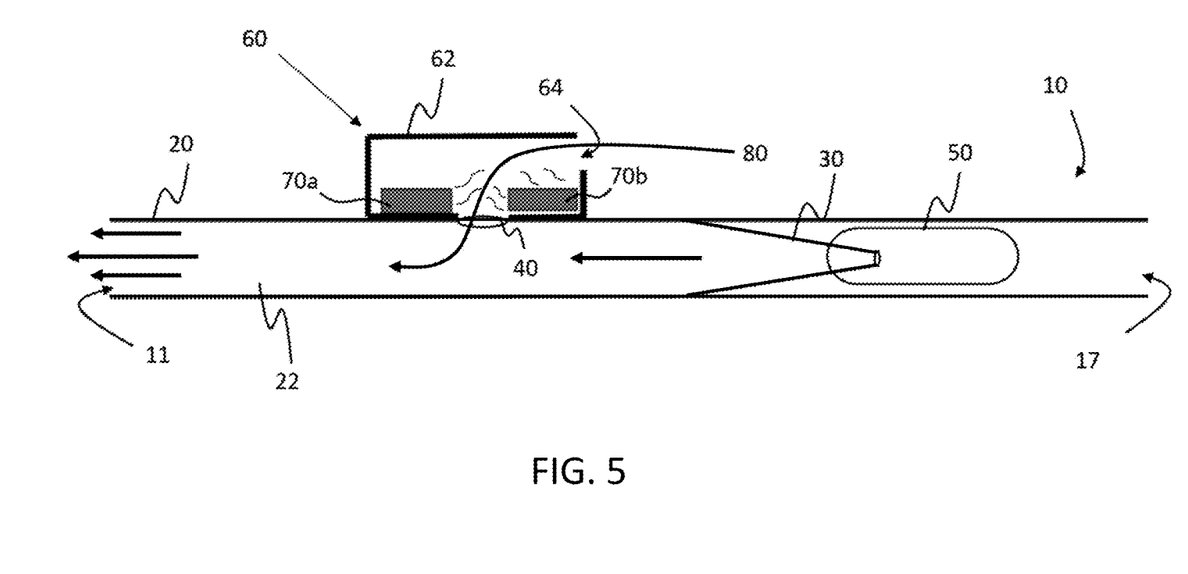
Figure 6:
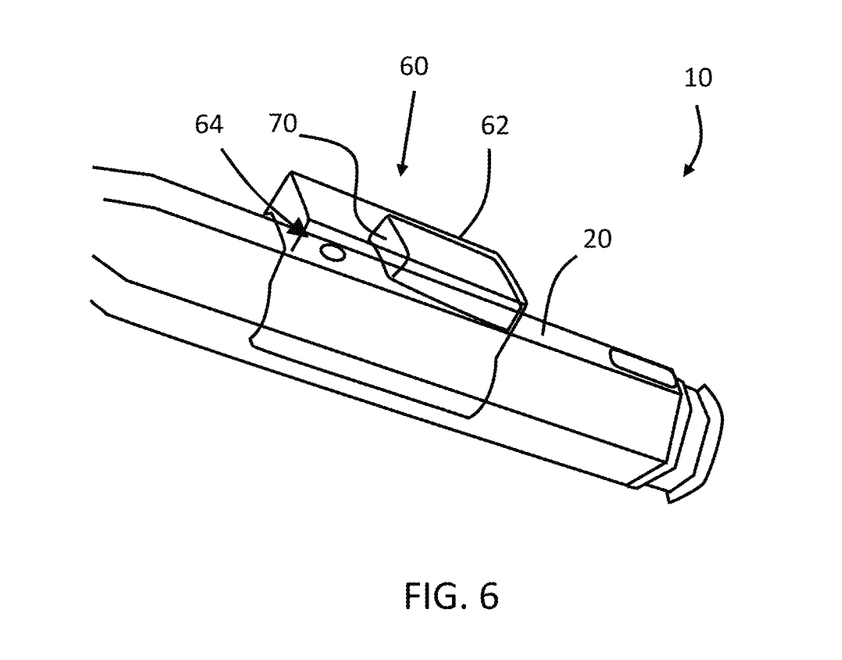

In certain embodiments, a single flavoring and/or cough suppressant component 70 is shaped to form a position distally, proximally, adjacent, or above opening 40 or device 10. In alternative embodiments, multiple flavoring and/or cough suppressant components 70 can be utilized for placement at various positions near opening 40. In the exemplary embodiment of FIG. 3, a single flavoring and/or cough suppressant component 70 is positioned distal of opening 40. In another example shown in the exemplary embodiment of FIG. 4, a flavoring and/or cough suppressant component is positioned proximal of opening 40. The example of FIG. 5 shows a first 70a and second 70b flavoring and/or cough suppressant component positioned on opposite sides of opening 40. Accordingly, components 70a and 70b may be the same or different type of flavoring and/or cough suppressant component. Combinations of these positions can be employed in alternate embodiments, as desired. Although a single inlet opening 64 is shown in FIGS. 3-5, as mentioned previously, multiple openings, or a filtered or porous opening, can be employed, as is true for outlet opening 66. Further, inlet openings 64 may be angled through the housing 62 or be formed of different sizes to promote a particular airflow of air during inhalation. Similar opening 64 patterns could be formed to increased airflow over the flavoring and/or cough suppressant component 70 for a more powerful flavoring and/or cough suppressant effect. A hinged or removable cap to any of openings 64 could also be used so that the flavoring and/or cough suppressant component does not dry out too quickly while not in use. A working example of the flavoring and/or cough suppressant compartment releasably attached to a dry powder inhaler is shown in FIG. 6.

Figure 7:
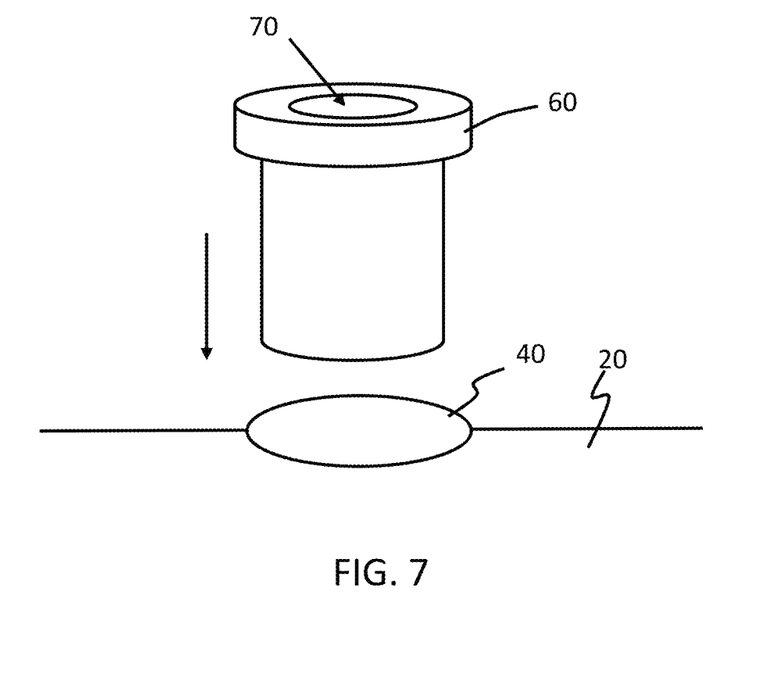

In still other embodiments, the compartment 60 may take the form of an insertable column, as shown in FIG. 7. As shown, compartment 60 may be generally cylindrical or otherwise suitably shaped to fit snugly into opening 40 of device 10. Compartment 60 may include a hollow passage or lumen running through its length, and the flavoring and/or cough suppressant component 70 may be positioned along at least a portion of the interior surfaces of the lumen. Accordingly, airflow from the exterior environment 5 may flow through the lumen of inserted compartment 60, such that at least a portion of the flavoring and/or cough suppressant component 70 is drawn into the proximal passage 22 of device 10. In this embodiment, the compartment 60 can protrude partially into passageways of the dry powder inhaler to further promote mixing with the internal airflow of the device. In a further embodiment, the lumen through compartment 60 may also include a pressure actuated elastomeric valve (such as a sleeve, duckbill or slit valve) that actuates in response to a threshold negative air pressure, such as a user inhalation.

In further embodiments, the flavoring and/or cough suppressant compartment may be engaged with the distal opening 17 of device 10. Accordingly, the flavoring and/or cough suppressant component 70 may be drawn into the same flow of air prior to entrainment of the medicament powder within capsule 50.

As would be appreciated by those having ordinary skill in the art, embodiments of the invention have applications that may extend beyond dry powder inhalers. For instance, vapor-type cigarettes and diagnostic inhalation systems such as bronchial provocation devices can also benefit from the invention as described throughout the embodiments.

An exemplary method for dry powder inhalation is as follows. In certain embodiments, the method includes the steps of providing a dry powder inhaler including a proximal end having a proximal opening, a distal end, and shaft wall extending from the proximal end to the distal end, a first compartment configured to hold a dry powder, a pathway connected to the first compartment by a first opening, the pathway including the proximal opening, and a second opening in the shaft wall connected to the pathway. In certain embodiment, the method provides a housing attachable to the shaft wall and configured to at least partially cover the second opening, the housing having first and second housing openings and at least one flavoring or cough suppressant component. The method may also include the step of generating a negative pressure at the proximal opening such that a portion of the dry powder exits the first compartment and enters the pathway, a portion of the at least one flavoring or cough suppressant component exits the housing and enters the pathway through the second opening, and the portion of the dry powder and the portion of the at least one flavoring or cough suppressant mix in an airflow generated by the negative pressure. In certain embodiments the dry powder comprises nicotine. Other medicaments could also be utilized. In certain embodiments, the negative pressure is generated by a user inhalation, although it could also be generated by a machine, such as in a diagnostic device. The housing is attachable and detachable to the shaft wall, thus, in certain embodiments, the method includes the step of detaching the housing from the shaft wall, and generating a second user inhalation generating an airflow comprising the dry powder. The user could optionally reattach the housing and generate a third user inhalation, or alternatively generate a third inhalation without reattaching the housing, depending on their preference for the flavor or cough suppressant. In certain embodiments, the portion of the dry powder and the portion of the at least one flavoring or cough suppressant mix at least partially within the pathway. In certain embodiments, the portion of the dry powder and the portion of the at least one flavoring or cough suppressant mix at least partially after exiting the proximal opening. In certain embodiments, they mix both before and after leaving the proximal opening, as part of a general mixing process in the airstream. In certain embodiment, the flavoring or cough suppressant component is a liquid contained within a wick positioned within the housing, either partially or fully. In certain embodiments, the flavoring or cough suppressant component comprises menthol.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A device for adding a flavor or cough suppressant component to an inhaler having a wall forming a tubular body with a length extending between a first end and a second end and an exterior surface with a side air inlet in the wall along the length, the device comprising:
    a housing having an interior chamber, wherein the housing includes at least one air inlet and at least one air outlet connected to the interior chamber, thereby forming an airflow path through the interior chamber; and
    at least one flavoring or cough suppressant component positioned within the interior chamber;
    the housing comprising an attachment mechanism comprising a snap fit, wherein the attachment mechanism comprises arms disposed at opposing sides of the housing, constructed to clip onto the exterior surface of the tubular body along the length of the inhaler such that the at least one air outlet of the device aligns with the side air inlet of the inhaler and such that the airflow path of the device is in fluid communication with the inhaler side air inlet.

2. The device of claim 1, wherein the flavoring or cough suppressant component is a powder.

3. The device of claim 1, wherein the flavoring or cough suppressant component is a liquid contained within a wick positioned within the interior chamber of the device.

4. The device of claim 1, wherein the flavoring or cough suppressant component comprises menthol.

5. A dry powder inhaler, comprising:
    a first housing having a tubular wall with a proximal end, a distal end and a length therebetween, wherein the housing defines an internal passage having proximal and distal regions along the length of the first housing; the first housing comprising:
        a proximal end opening forming a mouthpiece, a distal end opening, and a wall opening through a side of the tubular wall, each in connection with the internal passage; and
        a compartment within the distal region of the internal passage comprising a container of a dry powder; and
    a second housing having an interior chamber, wherein the second housing includes at least one air inlet and at least one air outlet connected to the interior chamber, thereby forming an airflow pathway through the interior chamber, and at least one flavoring or cough suppressant component positioned within the interior chamber, wherein the second housing comprises an attachment mechanism comprising a snap fit, wherein the attachment mechanism comprises arms disposed at opposing sides of the second housing, constructed to clip onto an exterior surface of the tubular wall along the length of the first housing such that the at least one air outlet of the second housing aligns with the wall opening of the first housing when the second housing engages the first housing.

6. The inhaler of claim 5, wherein the flavoring or cough suppressant component is a powder.

7. The inhaler of claim 5, wherein the flavoring or cough suppressant component is a liquid contained within a wick positioned within the interior chamber of the device.

8. The inhaler of claim 7, wherein the flavoring or cough suppressant component comprises menthol.

9. The inhaler of claim 8, wherein the inhaler is suitable for delivering the dry powder comprising nicotine as a medicament disposed within the compartment.

10. A dry powder inhaler system comprising:
    an inhaler housing comprising a tubular body comprising:
        a proximal end, a distal end, a length extending between the proximal and distal ends, an internal passage extending along the length through the body from a distal inlet opening to a proximal outlet opening, and a capsule disposed within the internal passage, the capsule containing a dry powder comprising a medicament;
    the tubular body defining an exterior surface and comprising a side opening between the proximal end and distal end; and
    a flavorant compartment comprising: a flavorant housing removably attached to the exterior surface of the tubular body at the side opening by an attachment mechanism comprising a snap fit, wherein the attachment mechanism comprises arms disposed at opposing sides of the flavorant housing, constructed to clip onto the exterior surface of the tubular body along the length, the flavorant housing forming an air inlet and an interior space, the air inlet and the interior space being in fluid communication with the internal passage of the inhaler housing via the side opening.

11. The dry powder inhaler system of claim 10, wherein the inhaler housing comprises a piercing element configured to pierce the capsule received in the inhaler housing.

12. The dry powder inhaler system of claim 10, wherein the flavorant compartment comprises a flavor element.

13. The dry powder inhaler system of claim 10, wherein the flavorant compartment comprises a cap covering the air inlet.

14. The dry powder inhaler system of claim 10, wherein the flavorant compartment comprises a cuboidal shape forming the interior space.

15. The dry powder inhaler system of claim 10, wherein the system is configured for simultaneous delivery of the dry powder disposed within the internal passage of the inhaler and a flavorant disposed within the flavorant compartment.

16. The dry powder inhaler system of claim 10, wherein the system comprises an airflow path with a first portion extending from the distal inlet opening to the internal passage of the inhaler, a second portion extending from the air inlet of the flavorant compartment to the internal passage of the inhaler via the side opening, and a third portion extending from the internal passage to the proximal outlet opening.

* * * * *